United States Patent [19]

Russell

[11] Patent Number: 4,737,143

[45] Date of Patent: Apr. 12, 1988

[54] CATHETER COUPLING AND ATTACHMENT ASSEMBLY

[76] Inventor: David A. Russell, Box 4000, Rawlins, Wyo. 82301

[21] Appl. No.: 861,880

[22] Filed: May 12, 1986

[51] Int. Cl.[4] .............................................. A61M 5/32
[52] U.S. Cl. ................................... 604/180; 604/174; 128/DIG. 26
[58] Field of Search ............... 604/174, 177, 179, 180; 128/133, DIG. 26

[56] References Cited

U.S. PATENT DOCUMENTS

| | | | |
|---|---|---|---|
| 4,059,105 | 11/1977 | Cutruzzula et al. | 604/180 |
| 4,224,937 | 9/1980 | Gordon | 604/180 |
| 4,275,721 | 6/1981 | Olson | 128/133 |
| 4,353,369 | 10/1982 | Muetterties et al. | 128/DIG. 26 |
| 4,460,356 | 7/1984 | Moseley | 604/180 |
| 4,484,913 | 11/1984 | Swauger | 604/179 |
| 4,490,141 | 12/1984 | Lacko et al. | 128/133 |

Primary Examiner—Stephen C. Pellegrino
Assistant Examiner—Ralph Lewis
Attorney, Agent, or Firm—Fields, Lewis, Pittenger & Rost

[57] ABSTRACT

A coupling and attachment assembly for catheters and the like includes two pairs of side body portions with adhesive coatings on the bottom surfaces and a coupling permanently attached to a central portion of the attachment member. The coupling has a coupling portion that easily connects to a complementary coupling portion on the inlet end of a catheter so the coupling can be connected to the catheter and the attachment member secured to the patient in a fast and efficient manner. An aseptic flap on the member covers the puncture after the catheter has been inserted. For some applications an intravenous line is connected to the inlet end of the coupling and for another there is a closure cap. An auxiliary strip is connected to the flow line to further secure the assembly to the patient.

15 Claims, 2 Drawing Sheets

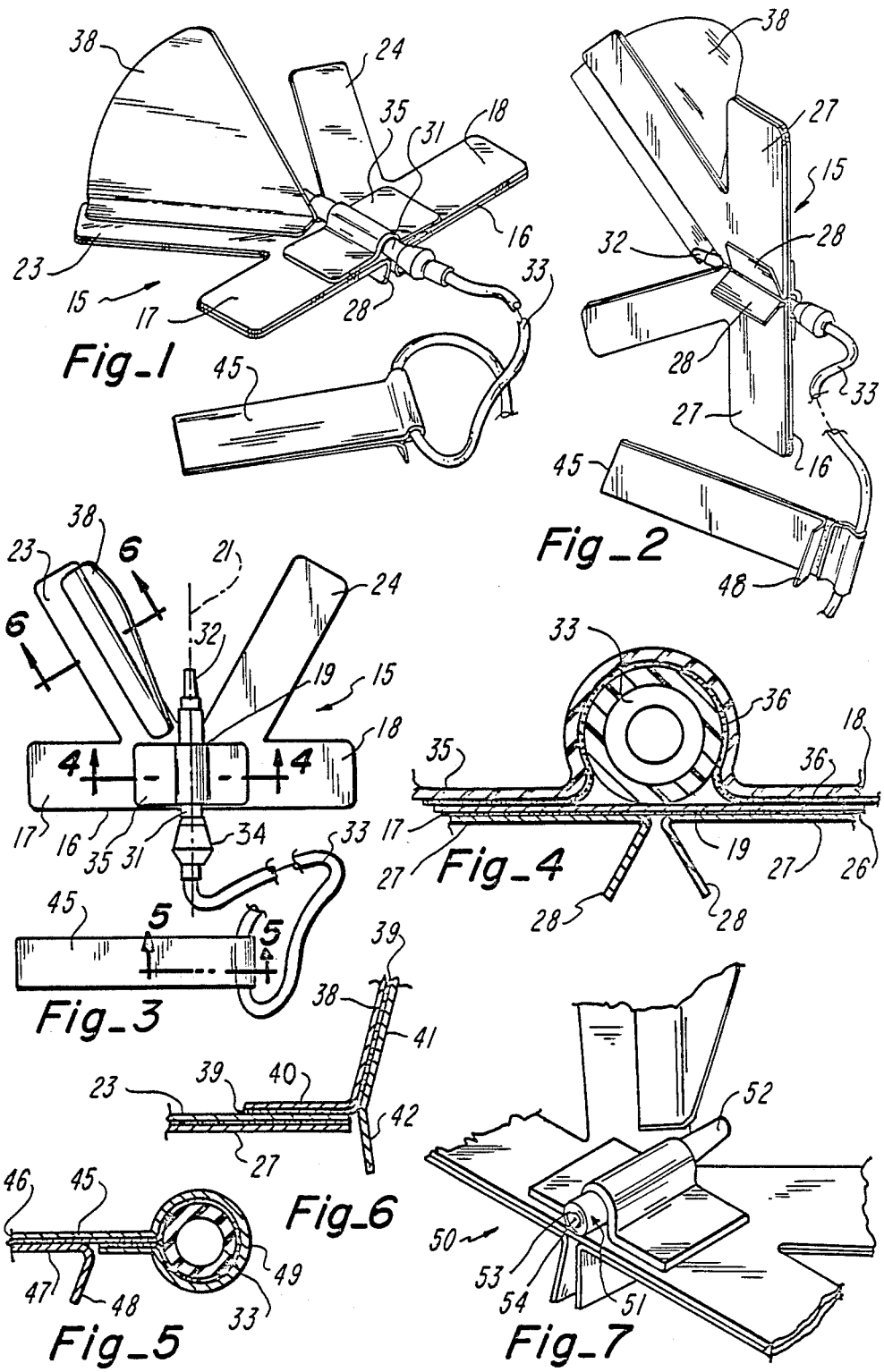

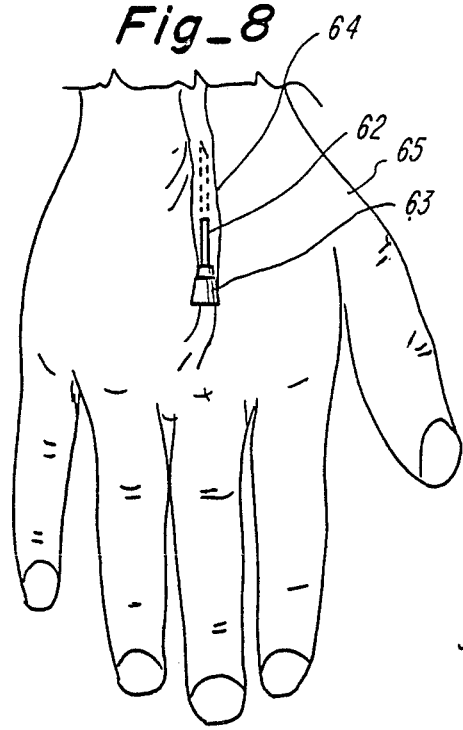
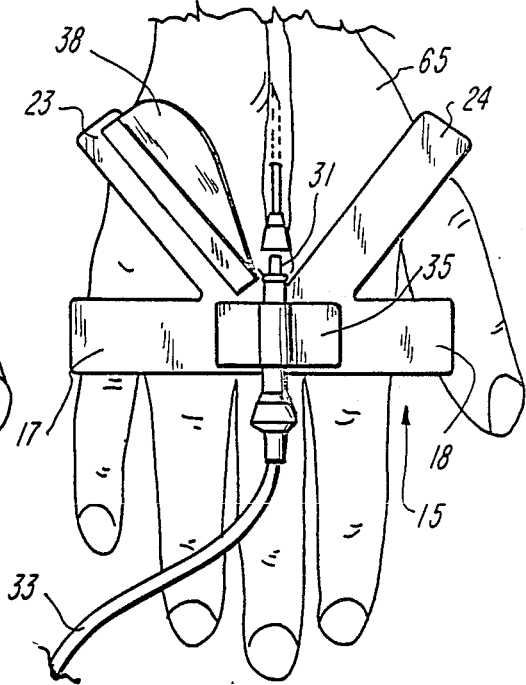
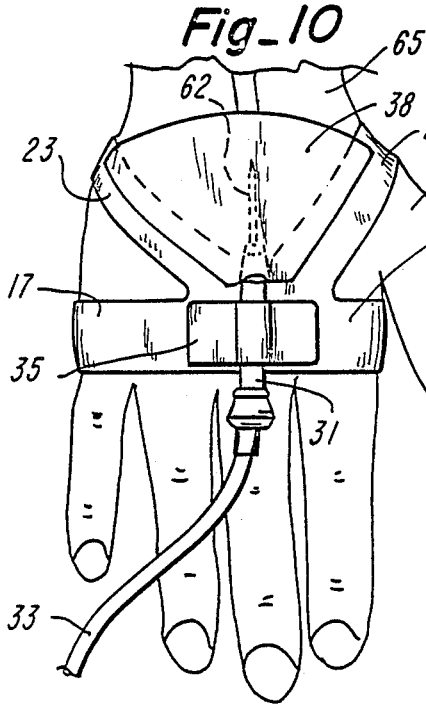
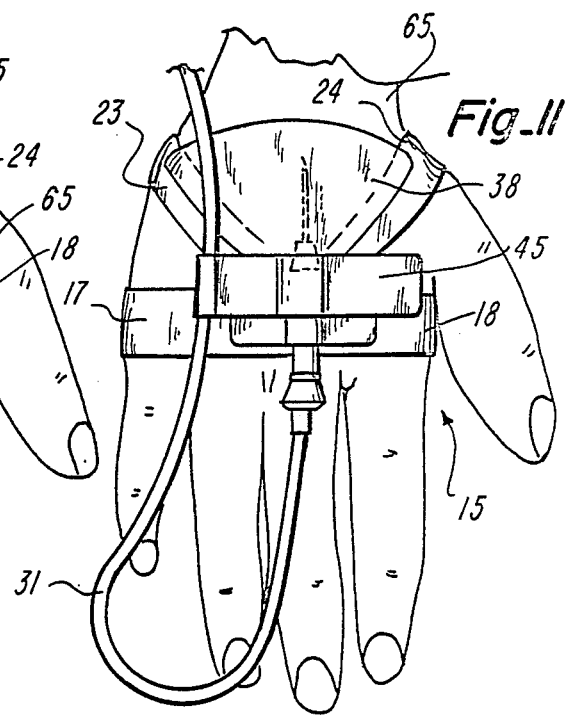

CATHETER COUPLING AND ATTACHMENT ASSEMBLY

TECHNICAL FIELD

This invention relates to a novel and improved assembly for firmly securing a catheter or like instrument to the skin of a patient.

BACKGROUND ART

In the past adhesive tape has been the most frequently used means for securing a catheter to a patient's body. The "chevron" taping technique has been used as an improved way to prevent the catheter from moving relative to the body of the patient. A number of attachment devices of a special construction have been proposed to secure the catheter to the patient.

Lacko et al U.S. Pat. No. 4,490,141 discloses an anchor tape device with an anchor portion having an adhesive on a lower surface of and a stabilizing portion including inclined wing segments having an adhesive on an upper surface. The device has a hole that receives the hub of the catheter. In use the inclined wing segments are folded back over the anchor portion.

Swauger U.S. Pat. No. 4,484,913 discloses a holder for a syringe having straight and inclined pairs of support members on opposite ends of a flat central base. One of the support members has a shaped recess for insertably receiving the syringe to releasably secure the syringe to the holder.

Moseley U.S. Pat. No. 4,460,356 discloses a precut anchor tape in which three separate strips are provided one of which is folded around the catheter to extend in inclined directions to secure the catheter in place on the patient.

DISCLOSURE OF INVENTION

A coupling and attachment assembly includes an attachment member having two pairs of outwardly extending side body portions with an adhesive on the bottom surface of each that fastens to the skin of the patient and a coupling permanently secured to a central body portion of this attachment member so that after the catheter is inserted into the patient the coupling slidably connects to the inlet end of the catheter and the attachment member is secured to the skin of the patient to firmly secure the catheter to the patient. An aseptic flap on the attachment member is used to cover the puncture and further secures the catheter in place.

BRIEF DESCRIPTION OF DRAWINGS

FIG. 1 is a top perspective view of a line coupling and attachment assembly embodying features of the present invention.

FIG. 2 is a bottom perspective view of the assembly shown in FIG. 1.

FIG. 3 is a top plan view of the assembly.

FIG. 4 is a sectional view taken along lines 4—4 of FIG. 3.

FIG. 5 is a sectional view taken along lines 5—5 of FIG. 3.

FIG. 6 is a sectional view taken along lines 6—6 of FIG. 3.

FIG. 7 is a fragmenting top perspective view of another form of coupling and attachment assembly.

FIG. 8 is a top plan view of the catheter needle in place penetrating the skin of the back of the hand of a patient.

FIG. 9 is a top plan view with the assembly prior to hooking the line coupling to the catheter or securing the pairs of side portions to the hand.

FIG. 10 is a top plan view with the assembly firmly coupled to the line coupling and secured to the hand.

FIG. 11 is a top plan view of an auxiliary strip further securing the line and line coupling to the hand.

DETAILED DESCRIPTION

Referring now to the drawings there is shown a line coupling and attachment assembly 15 which includes an attachment member 16 having a pair of oppositely extending flap-like side body portions 17 and 18 extending laterally out from a central body portion 19 having a center line 21. There is further provided a second pair of oppositely extending flap-like side body portions 23 and 24 also referred to as inclined side body portions displaced along central body portion 19 from the first-mentioned pair and extending diagonally at an angle from the center line of approximately 30 degrees and from the adjacent side body portion an angle of approximately 60 degrees. The side body portions are symmetrically arranged about the center line 21 so there is a mirror image on each side of the center line.

Both the pairs of side body portions have an adhesive coating 26 on the bottom surface which is covered by a backing strip 27 until it is applied to the patient. The backing strip 27 is split along center line 21 into two backing strip sections and folded back along adjacent edges to form a pair of folded edge portions 28 that extend beyond the attachment member to be gripped by the person applying assembly 15 to remove the backing strip sections. Each backing strip section is removed when the attachment member is ready to be secured to the skin of the patient.

A line coupling 31 has a male coupling portion 32 at one end and a flow line 33 connected to the opposite end. The line coupling 31 is a rigid clear plastic section and is shown as having a hollow flexible injection bulb 34 between the rigid section and the tubing 33. The flow line 33 typically will be the clear plastic tubing of an intravenous (I. V.) set such as a VENOSET® Piggyback with CAIR® clamp model no. 4967. The line coupling 31 is also commonly referred to as a male adapter. This construction also allows for an extension line to be readily added between the coupling 31 and the male adapter of a conventional I. V. set. The line coupling 31 is securely fastened to the central body portion 19 by a flexible strip 35 having an adhesive coating 36. The strip 35 shown is flexible and conforms to the circular shape of the line coupling 31 to form an annular segment around the coupling 31. A material found particularly suitable for strip 35 is a foam 3M adhesive tape surgical spec. no. 1772-OEM-2. It is understood that other annular hubs or bodies such as a rigid section of plastic tubing stapled or otherwise secured to member 16 may be used in place of strip 35 for attachment purposes.

A generally V-shaped aseptic cover or flap 38 is attached to inclined side portion 23. An adhesive coating 39 is provided on the lower surface of flap 38. An edge portion 40 has the adhesive coating pressed against the top of the inclined side portion 23 to secure flap 38 to side portion 23. The cover or flap 38 primarily serves to cover the puncture but also further secures the catheter in place. A backing strip 41 covers the remaining part of the coating 39, until the device is applied. An edge portion 42 of the backing strip is folded back and extends beyond the attachment member for gripping to remove the backing strip 41 when required. The aseptic cover provides an immediate and time saving aseptic technique for both a bustling emergency room and the roughest ambulance field condition.

An auxiliary fastening strip 45 has an adhesive coating 46 on the bottom surface and a backing strip 47 with an edge portion 48 folded back. This auxiliary strip 45 has one end portion folded back around the line 33 at a fold loop with end loop portion 49 connecting to the main body of strip 45 and fastens to the patient to further secure the flow line 33 to the patient as is described more fully hereafter. A material found particularly suitable for member 16, flap 38 and strip 45 is a foam 3M transpore surgical spec. no. 1527 L-OEM-2.

Referring now to FIG. 7 there is shown a coupling and attachment assembly 50 similar in construction to assembly 15 above described but with a modified coupling 51 that has a male coupling portion 52 at the front end to connect to the catheter and a closure cap portion 53 at the rear end with a dimple 54 into and through which a needle may be inserted to pass a fluid such as a medicament through the catheter and into the vein of the patient. The cap portion 53 is frequently referred to in the trade as a "Buffalo Cap".

Referring now to FIG. 8 there is shown a conventional catheter 62 having a female coupling portion 63 at the inlet end opposite the tapered pointed outlet end. The catheter 62 is shown as having been inserted into the vein 64 of the hand 65 of a patient. The male coupling portion 32 is slidably inserted into the female coupling portion 63 to form a fluid-tight flow connection therebetween.

By way of example and not limitation the dimensions of the above described assembly are as follows full width of 15—12 cm
full length of 15—8 cm
length of 23, 24 from edge of 17, 18 respectively—6 cm
width of 17, 18—2.5 cm
width of 23, 24—2 cm In a full sequence for applying the assembly 15 to a patient, the vein 64 into which the catheter 62 is to be inserted is catheterized as in the conventional procedure. The tapered outlet end of the catheter is advanced into the vein using a stylett in the conventional manner and the stylett is discarded. The male coupling portion 32 is inserted into the female coupling portion 63 of the catheter 62 and good flow is established through the flow line.

The backing strip 27 is removed from both pairs of the side body portions and one at a time they are secured to the patient by pressing the adhesive coating 36 firmly against the skin of the patient.

The adhesive backing strip 41 is then removed from the aseptic flap 38 and the adhesive coating, 39 is pressed over the joined coupling portions 52 and 63, catheter and the venipuncture site in the hand.

The backing strip 47 is removed from the auxiliary strip 45 and pressed against the skin with the flow line 33 looped back to further prevent the inserted catheter 62 from becoming dislodged.

The assembly is specifically adapted to be applied to the limbs such as hand, arm or leg and in each case the side portions do not extend all the way around the limb so as to inhibit circulation.

From the foregoing it should be apparent that the application of the above described assembly is considerably faster than other devices and methods for securing intravenous lines thereby saving a rescuer in the field or a nurse in the emergency room time in terms of minutes. The assembly is as easy to install as a band-aid. The catheter remains free for the necessary manipulation for a troublesome intravenous start.

The size and configuration of the assembly fits all anatomically popular intravenous catheter locations performing a high quality adhesive function without extending a full 360 degrees or being circumferential around the limb to which it is applied.

The assembly provides for stabilizing both the flow line or tubing and the catheter as a unit without hampering the integrity or function of either. There is less manipulation of the patient than securing methods which involve tape.

Although the present invention has been described with a certain degree of particularity, it is understood that the present disclosure has been made by way of example and that changes in details of structure may be made without departing from the spirit thereof.

What is claimed is:

1. A coupling and attachment assembly for catheters and the like comprising:
    an attachment member including a first pair of side body portions extending laterally out from a center line and a second pair of inclined side body portions extending diagonally out at an angle to said center line, said first and second pairs of side body portions being integral and a part of a single body, said side body portions having an adhesive coating on a bottom surface to secure said attachment member to the skin of a patient,
    a coupling for a catheter having a first coupling portion at an outlet end adapted to couple to a second coupling portion on the inlet end of a catheter, said first coupling portion being releasably coupled to said second coupling portion during use, said coupling being permanently attached to said attachment member to firmly secure a catheter inserted into a patient to said patient after said first and second coupling portions are joined together, said coupling adapted to receive a fluid at an inlet end for passage through the coupling and out said outlet end and through the catheter.

2. An assembly as set forth in claim 1 wherein said coupling has a flow line connected opposite said first coupling portion to deliver fluids to said coupling.

3. An assembly as set forth in claim 1 wherein said flow line is an intravenous tubing of an intravenous set.

4. An assembly as set forth in claim 1 wherein said coupling has an end closure cap opposite said first coupling through which a needle may be passed to transfer fluid to said catheter via said coupling.

5. An assembly as set forth in claim 1 wherein said side portions are limited in extent so they do not extend extirely around the limb of a patient to which they are secured.

6. An assembly as set forth in claim 1 wherein said first pair of side body portions and second pair of side body portions are symmetrically arranged about said center line so said member has mirror images on opposite sides of said center line.

7. An assembly as set forth in claim 1 wherein said attachment member has a backing strip that covers said adhesive coating and is removed when the attachment member is ready for being applied to the patient.

8. An assembly as set forth in claim 1 including an annular segment centered on said center line and permanently attached to said attachment member through which said coupling extends and is permanently attached.

9. An assembly as set forth in claim 8 wherein said annular segment is provided by a flexible strip having an adhesive coating on one surface that extends around a portion of the circumference of said coupling extends generally transverse to said center line and is pressed against the top surface of said attachment member along said first pair of side body portions.

10. An assembly as set forth in claim 1 further including an aspectic flap carried on said attachment member to cover the puncture provided by said catheter extending into the vein of a patient.

11. A coupling and attachment assembly for catheters and like instruments comprising:
an attachment member including a first pair of oppositely extending flap-like side body portions extending laterally out from a central body portion having a longitudinal center line and a second pair of oppositely extending opposed flap-like inclined side body portions displaced along said central body portion from said first pair and extending diagonally out at an angle to said longitudinal center line, said first and second pairs of side body portions being integral and a part of a single body, said side body portions having an adhesive coating on a bottom surface to secure said attachment member to the skin of a patient,
a coupling for a catheter having a first coupling portion at an outlet end adapted to couple to a second coupling portion on the inlet end of a catheter, said first coupling portion being releasably coupled to said second coupling portion during use, said coupling being permanently attached to said central body portion to firmly secure a catheter inserted into a patient to said patient when said first and second coupling portions are joined together, said coupling adapted to receive a fluid at an inlet end for passage through the coupling and out said outlet end and through the catheter, and
an aseptic flap on said attachment member to cover a puncture formed by said catheter in the patient and the space between said inclined side body portions.

12. A line coupling and attachment assembly for catheters and like instruments comprising:
an attachment member including a first pair of oppositely extending flap-like side body portions extending laterally out from a central body portion having a longitudinal center line and a second pair of oppositely extending opposed flap-like inclined side body portions displaced along said central body portion from said first pair and extending diagonally out at an angle to said longitudinal center line, said first and second pairs of side body portions being integral and a part of a single body, said side body portions having an adhesive coating on a bottom surface to secure said attachment member to the skin of a patient,
a line coupling for a catheter having a fluid flow line extending from an outlet end and a first coupling portion at a free end adapted to couple to a second coupling portion on the inlet end of a catheter, said first coupling portion being releasably coupled to said second coupling portion during use, said line coupling being firmly secured to said central body portion to secure a catheter inserted into a patient when said first and second coupling portions coupled together, said coupling adapted to receive a fluid at an inlet end for passage through the coupling and out said outlet end through the catheter, and
an aseptic flap on said attachment member to cover the puncture provided by the catheter extending into the vein of a patient.

13. An assembly as set forth in claim 12 further including an auxiliary strip having an adhesive coating on a bottom surface, said auxiliary strip being connected to said flow line a distance from said coupling to further secure said flow line to the skin of a patient.

14. A coupling and attachment assembly for catheters and like instruments comprising:
an attachment member including a first pair of oppositely extending flap-like side body portions extending laterally out from a central body portion having a longitudinal center line and a second pair of oppositely extending opposed flap-like inclined side body portions displaced along said central body portion from said first pair and extending diagonally out at an angle to said longitudinal center line, said side body portions having an adhesive coating on a bottom surface to secure said attachment member to the skin of a patient,
a coupling having a first coupling portion at an outlet end adapted to couple to a second coupling portion on the inlet end of a catheter, said coupling being permanently attached to said central body portion to firmly secure a catheter inserted into a patient to said patient when said first and second coupling portions are joined together, and
an aspetic flap on said attachment member to cover a puncture formed by said catheter in the patient and the space between said inclined side body portions, said aspectic flap having an adhesive coating along one edge portion that is pressed against an upper surface of one of said second pair of side body portions to secure said aspectic flap to said attachment member.

15. An assembly as set forth in claim 14 wherein said flap is generally V-shaped and covers a distance greater than the space between said second side body portions so that the adhesive coating is pressed against a portion of the top surfaces of both of said second side body portions in the covering position.

* * * * *